United States Patent [19]

Voth et al.

[11] Patent Number: Plant 5,263

[45] Date of Patent: Jul. 24, 1984

[54] STRAWBERRY PLANT 'PARKER'

[75] Inventors: Victor Voth, Santa Ana; Royce S. Bringhurst, Davis, both of Calif.

[73] Assignee: The Regents of the University of California, Berkeley, Calif.

[21] Appl. No.: 452,697

[22] Filed: Dec. 23, 1982

[51] Int. Cl.[3] ..... A01H 5/03

[52] U.S. Cl. ..... Plt./48

[58] Field of Search ..... Plt./48

*Primary Examiner*—Robert E. Bagwill

*Attorney, Agent, or Firm*—Townsend and Townsend

[57] ABSTRACT

A new and distinct variety of strawberry plant of the short-day type charcterized by fruit production as early as 'Tufts' or 'Tioga' and persistence in fruiting later than 'Douglas'. The variety performs well in both summer and winter plantings in south and central coastal California. Early fruit of the variety tends to be malformed similar to 'Tufts' and ranges from long conic to long flat wedgy in shape; seldom hollow internally with flesh uniform in color. The variety is further characterized by its small and reflexed calyx borne on a distinct neck and by the extreme firmness and durability of its fruit which in size is as large as 'Douglas'. Fruit flavor is comparable to most California varieties in current use and the variety is suitable for both fresh market and processing.

3 Drawing Figures

DESCRIPTION

This invention relates to a new and distinctive short-day type strawberry cultivar designated as 'Parker' which is the result of a cross between 'Douglas' (U.S. Plant Pat. No. 4,487) and Cal 71.98-605 (not patented) made in 1977. The pedigree is as follows:

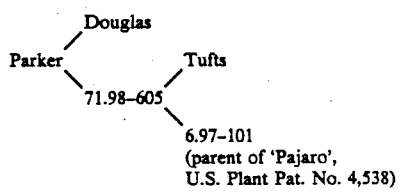

'Parker' first fruited at the University of California South Coast Field Station, Santa Ana in 1979 where it was selected and designated originally as Cal 77.30-605. It was tested later as advanced selection C3.

'Parker' has been propagated asexually by runners and has been tested at various University of California field stations and facilities and to a very limited extent in a few growers' fields under Test Agreement.

Figure 1:
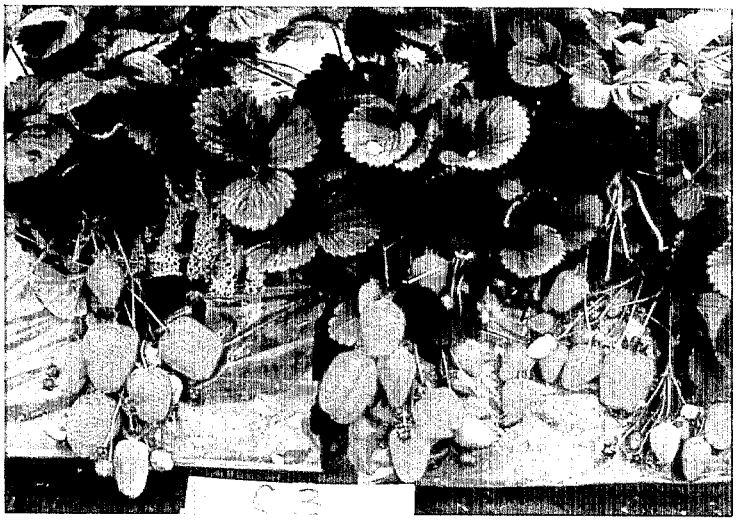
FIG. 1 shows typical growth, flowering and fruiting characteristics of the plant.
Figure 2:
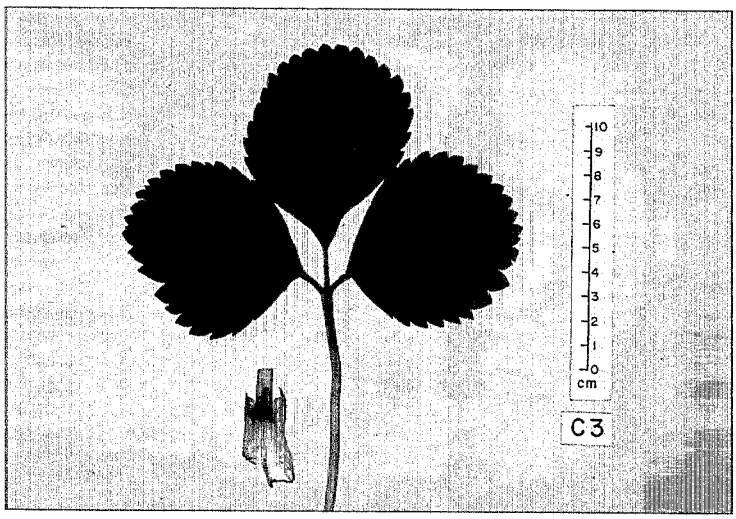
FIG. 2 shows a typical midsummer mature leaf from a plant in full fruit.
Figure 3:
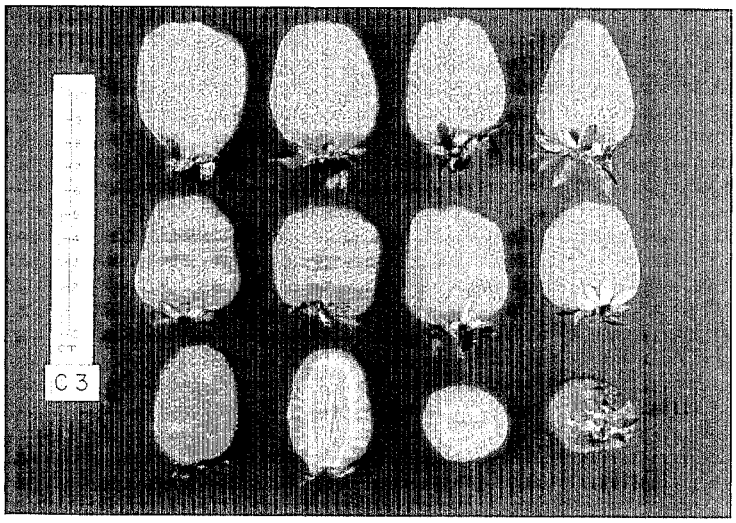
FIG. 3 shows representative early-season fruit with longitudinal and cross-sectional views.

'Parker' has performed well in winter and summer planting experiments, in south and central coastal California. It is about as early as 'Tufts' or 'Tioga', later than 'Douglas'. It tends to persist in fruiting later than 'Tufts', 'Tioga' or even 'Douglas'.

PLANTS AND FOLIAGE

'Parker' plants are semi-erect in growth habit, about the same size somewhat larger than those of the standard 'Tioga' in both winter and summer plantings as estimated by measuring petiole length on plants in full fruit. Leaflets of 'Parker' are about the same size as those of 'Tioga' with about the same number of serrations. Leaves are similar in color but slightly less intense than those of 'Tioga'; 2.5GY55 vs 2.5GY4/3 respectively (Munsell Color System-Nickerson Color Fan). Runner production in nursery plantings is very good, better than 'Tioga'. 'Parker' plants have a low chilling requirement, similar to 'Tioga' or 'Tufts'.

ISOZYMES IN LEAF EXTRACTS

'Parker' has been classified for three enzyme systems: (A.) Phosphoglucoisomerase (PGI); (B.) Leucine amino peptidase (LAP); and (C.) Phosphoglucomutase (PGM); making it identical to 'Aiko' but different from 'Tioga', 'Tufts', 'Douglas' or 'Pajaro' (below):

| | 'Tioga' | 'Tufts' | 'Douglas' | 'Pajaro' | 'Parker' & 'Aiko' |
|---|---|---|---|---|---|
| PGI | A1 | A2 | A3 | A4 | A4 |
| LAP | B1 | B3 | B3 | B3 | B3 |
| PGM | C3 | C4 | C1 | C1 | C2 |

*1981 J. Amer. Soc. Hort. Sci 106: 684–687.

FLOWERING AND FRUITING

'Parker' flowers are borne on long, semi-erect peduncles which are brought down quickly by the weight of the fruit. The flowers are self fertile with ample pollen throughout the season but part of the early fruit tends to be malformed similar to 'Tufts'.

FRUIT APPEARANCE

'Parker' fruit is long conic to long flat wedgy. Internally the fruit is solid throughout and seldom hollow. The fruit skin color is about 7R4.5/13 (ibid), slightly darker than that of fully colored 'Tioga', (about 7.5R4.5/13). The finish is glossy and attractive. The flesh is the same color, uniform throughout. The achenes are bright yellow and positioned flush with surface. The calyx is small in size borne on a distinct neck and reflexed. The fruit is extremely firm and more durable than that of 'Tioga', 'Tufts' or 'Aiko' according to penetrometer readings and handling comparisons.

The fruit size averages about as large as that of 'Douglas' with a wider range in size as the season advances.

FRUIT QUALITY

'Parker' has averaged about the same ascorbic acid content (24 mg/100 g fresh fruit) as 'Tioga' (23 mg) as tested on summer and winter plantings during 1981 and 1982 by the method of Loeffler and Ponting (1942, J. Indust. and Engin. Chem. 14:846). Soluble solids readings were not significantly different from those of 'Tioga', 'Tufts', 'Douglas', 'Aiko' or 'Pajaro' from comparable plantings. The flavor of 'Parker' is good, comparable to that of most of the cultivars now used in California in our opinion and according to most who have tried it. Some will object to the extreme firmness. It is suitable for fresh market and processing.

We claim:

1. The new and distinct variety of strawberry plant herein described and illustrated and identified by the characteristics enumerated above.

* * * * *